United States Patent
Hill et al.

(10) Patent No.: US 10,548,610 B2
(45) Date of Patent: Feb. 4, 2020

(54) APPARATUS AND METHODS FOR CLOSING VESSELS

(71) Applicant: VENOVATION INC., Santa Clara, CA (US)

(72) Inventors: Bradley B. Hill, Santa Clara, CA (US); James Hong, Sunnyvale, CA (US); Wenkang Qi, Cupertino, CA (US)

(73) Assignee: VENOVATION INC., Santa Clara, CA (US)

( * ) Notice: Subject to any disclaimer, the term of this patent is extended or adjusted under 35 U.S.C. 154(b) by 1004 days.

(21) Appl. No.: 14/606,892

(22) Filed: Jan. 27, 2015

(65) Prior Publication Data

US 2015/0201947 A1    Jul. 23, 2015

Related U.S. Application Data

(63) Continuation of application No. PCT/US2013/052432, filed on Jul. 27, 2013.
(Continued)

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/1227* (2013.01); *A61B 17/12031* (2013.01);
(Continued)

(58) Field of Classification Search
CPC ............ A61B 17/1285; A61B 17/1227; A61B 17/12109; A61B 17/12145;
(Continued)

(56) References Cited

U.S. PATENT DOCUMENTS 5,662,657 A * 9/1997 Carn ................... A61F 2/30723
606/92
8,075,568 B2 * 12/2011 Selis ..................... A61B 19/54
600/431
(Continued)

FOREIGN PATENT DOCUMENTS

JP          03127252       11/2006
JP       2008513052 A      5/2008
(Continued)

OTHER PUBLICATIONS

Korean Intellectual Property Office; International Search Report and Written Opinion for corresponding International Application No. PCT/US2013/052432, dated Nov. 11, 2013, 13 pages.
(Continued)

*Primary Examiner* — Erich G Herbermann
(74) *Attorney, Agent, or Firm* — William A. English; Vista IP Law Group LLP

(57) ABSTRACT

Apparatus and methods are provided for closing a tubular structure within a patient's body. The apparatus includes a needle including a proximal end including a hub, a distal end including a sharpened distal tip, a lumen having an oblong cross-section extending proximally from the distal end, and defining a longitudinal axis between the proximal and distal ends, and a clip deliverable from the lumen. The clip is compressible between a relaxed state in which a plurality of tines of the clip are shaped to engage and close a tubular structure within a patient's body, and a stressed state in which the tines are compressed to allow the clip to be loaded into the. The apparatus may also include a pusher member for deploying the clip from the distal tip of the needle such that the tines engage and close a tubular structure through which the tubular member is directed.

14 Claims, 14 Drawing Sheets

Related U.S. Application Data

(60) Provisional application No. 61/676,551, filed on Jul. 27, 2012.

(51) Int. Cl.
*A61B 17/122* (2006.01)
*A61B 17/064* (2006.01)
*A61B 17/06* (2006.01)
*A61B 17/068* (2006.01)
*A61B 18/14* (2006.01)
*A61B 18/00* (2006.01)
*A61B 90/00* (2016.01)

(52) U.S. Cl.
CPC .. *A61B 17/12109* (2013.01); *A61B 17/12145* (2013.01); *A61B 17/068* (2013.01); *A61B 18/1477* (2013.01); *A61B 2017/061* (2013.01); *A61B 2017/0641* (2013.01); *A61B 2017/0645* (2013.01); *A61B 2017/0647* (2013.01); *A61B 2017/0649* (2013.01); *A61B 2017/1205* (2013.01); *A61B 2018/00595* (2013.01); *A61B 2090/034* (2016.02)

(58) Field of Classification Search
CPC ............ A61B 17/12031; A61B 17/068; A61B 18/1477; A61B 2017/061; A61B 2017/0641; A61B 2017/0645; A61B 2017/1205; A61B 2017/0647; A61B 2090/034; A61B 2017/0649; A61B 2018/00595
See application file for complete search history.

(56) References Cited

U.S. PATENT DOCUMENTS

| | | | |
|---|---|---|---|
| 2002/0087170 A1* | 7/2002 | Kuhns | A61B 17/064 606/143 |
| 2002/0165561 A1* | 11/2002 | Ainsworth | A61B 17/0469 606/151 |
| 2003/0105473 A1* | 6/2003 | Miller | A61B 17/064 606/139 |
| 2010/0217306 A1 | 8/2010 | Raabe et al. | |
| 2012/0283758 A1 | 11/2012 | Miller et al. | |
| 2013/0046331 A1 | 2/2013 | Christensen et al. | |
| 2013/0226201 A1 | 8/2013 | Miller et al. | |
| 2014/0243857 A1 | 8/2014 | Miller et al. | |

FOREIGN PATENT DOCUMENTS

| | | |
|---|---|---|
| JP | 2010081970 A | 4/2010 |
| JP | 2010178897 A | 8/2010 |
| JP | 2011520570 A | 7/2011 |
| WO | 2009143291 A1 | 11/2009 |

OTHER PUBLICATIONS

European Patent Office; Search Report and Office Action communications for corresponding European Patent Application No. 13822922.4, dated Jun. 30, 2017, 39 pages.

Japanese Patent Office; Numata, Kiyoshi and Takaoka, Ryoichi, Office Action and Response for corresponding Japanese Patent Application No. 2015-524500, dated Apr. 18, 2017, 20 pages.

* cited by examiner

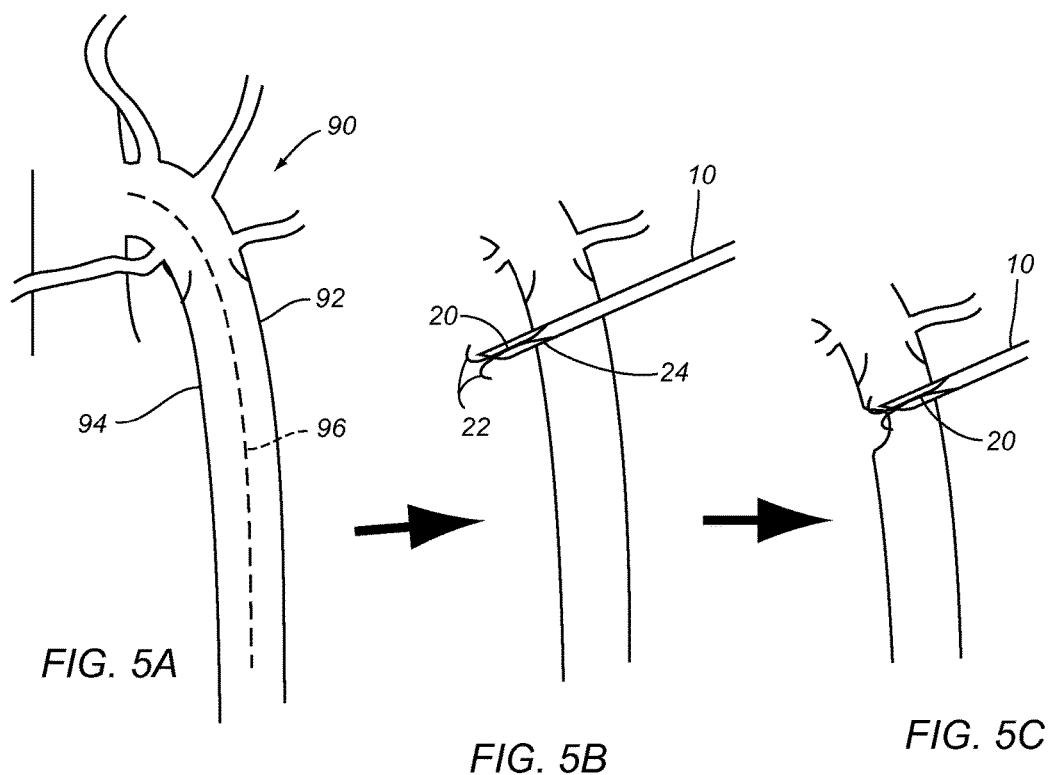
*FIG. 5A*  *FIG. 5B*  *FIG. 5C*
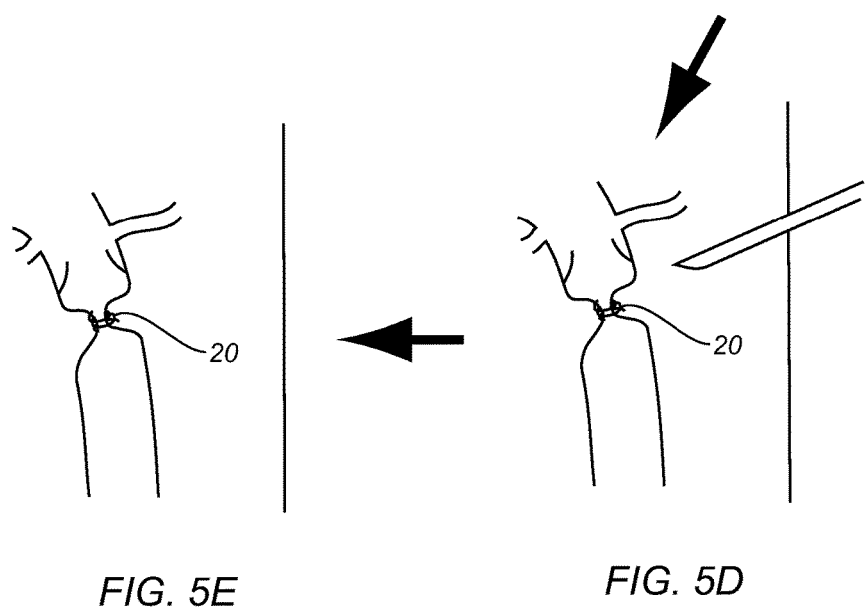
*FIG. 5E*  *FIG. 5D*

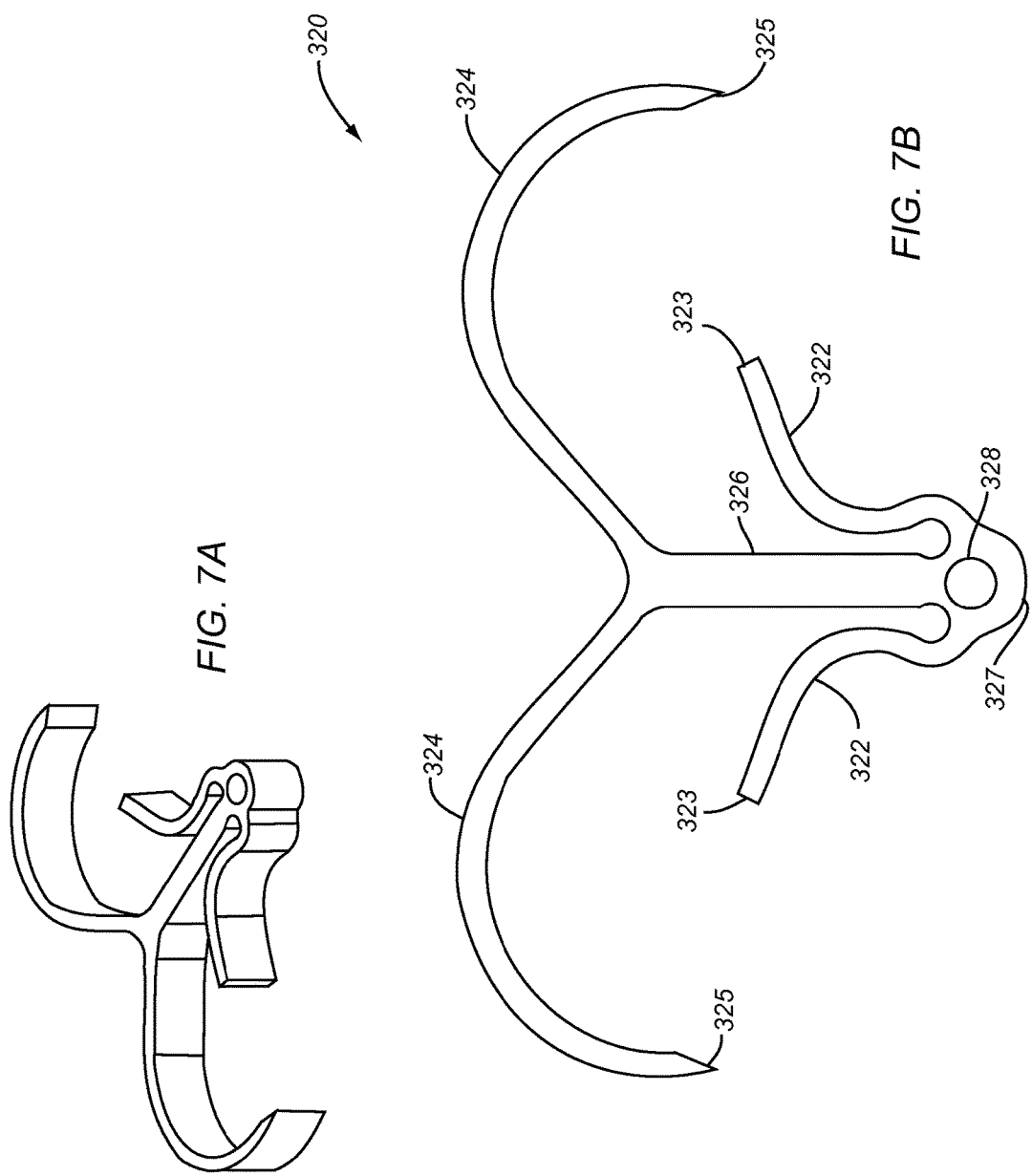

APPARATUS AND METHODS FOR CLOSING VESSELS

RELATED APPLICATION DATA

The present application is a continuation of co-pending International Application No. PCT/US2013/052432, filed Jul. 27, 2013, which claims the benefit of U.S. provisional application Ser. No. 61/676,551, filed Jul. 27, 2012, the entire disclosures of which are expressly incorporated by reference herein.

FIELD OF THE INVENTION

The present invention relates to apparatus, systems, and methods for closing blood vessels or other tubular structures within a patient's body. More specifically, the present invention is directed to apparatus and methods for closing veins or other tubular structures in a patient's body, e.g., by delivering one or more clips into, through, and/or around the tubular structure.

BACKGROUND

Mild vein-related abnormalities are common and affect most adults. More severe disease with visible varicose veins occurs in up to forty percent (40%) of men and women. Chronic venous insufficiency occurs in about two percent (2%) of the U.S. population and can cause swelling, stasis pigmentation, scarring of the skin and underlying tissues, and skin ulceration in advanced cases. The incidence of all venous disease increases with advancing age.

The causes of varicose vein disease are varied. A family history is common and a genetic predisposition may play a factor. Obstruction of the main draining veins of the leg due to blood clots, called deep venous thrombosis or DVT, and loss of valve function or "valvular incompetence" are the main causes of varicose veins and most forms of venous insufficiency.

Patients with advanced disease are often unable to continue their customary employment, and they may become temporarily or permanently disabled from lack of mobility. The economic and psychological effects can be profound for these patients.

Patients who have varicose veins or more serious forms of venous insufficiency caused by valvular incompetence of the saphenous vein can be managed in a variety of ways. The first line of therapy in most cases is compression therapy and leg elevation. These noninvasive measures can help alleviate symptoms and heal ulcers in some instances. Oftentimes, patients are unable to tolerate tight compression garments and they may not be able to elevate the extremity for an adequate time to relieve symptoms and promote ulcer healing because of work requirements and/or other lifestyle issues.

Invasive treatment methods for disease stemming from valvular incompetence of the saphenous vein include: 1) vein stripping, 2) high-ligation, 3) foam sclerotherapy, and 4) endovenous ablation. Vein stripping and high-ligation have fallen out of favor because stripping is traumatic and high-ligation is associated with a high recurrence rate. Foam sclerotherapy has not had widespread adoption and is known to cause visual disturbance (scotoma), migraine-like headache, cough, and neurologic deficit (usually transient) in less than two percent (2%) of cases.

In recent years, endovenous ablation using radiofrequency energy or laser energy has become the preferred treatment for patients who suffer from venous disease due to axial reflux in the long and short saphenous veins and in some cases involving reflux in the perforating veins. However, endovenous ablation requires tumescent anesthesia and is typically done in an ambulatory surgery setting. Even though the procedure is minimally invasive, some patients experience significant bruising and post-procedural pain, which may last for more than a week. Endovenous ablation involves destruction of the vein from the inside out along the full length of the treatment segment. The tissue destruction causes pain in the soft tissues after the anesthetic wears off. Some patients require prescription pain medications and often several days off work until the pain has resolved.

Therefore, there is a need for improved systems for treating venous insufficiency caused by valvular incompetence of the saphenous vein.

SUMMARY

The present invention is directed to apparatus, systems, and methods for closing a tubular structure, e.g., a blood vessel, such as a saphenous or other vein, to eliminate flow of fluid through the lumen of the tubular structure. In addition, the present invention is directed to apparatus and methods for delivering one or more clips into a patient's body, e.g., percutaneously, to close tubular structures.

The description herein focuses on using various apparatus and methods to close a saphenous vein, e.g., for treatment of valvular incompetence. It will be appreciated that other tubular structures may also be closed using the apparatus and methods described herein. For example, other structures that may be treated include arteries, biliary tubes, bronchial or other airway tubes, or other anatomical structures, including prosthetic tubular grafts, e.g., as are used in vascular bypass operations.

One common method for treating saphenous vein reflux, e.g., caused by valvular incompetence at the region of the saphenofemoral junction, where the long saphenous vein proximally empties into the common femoral vein in the groin area, is called "high-ligation" of the saphenous vein. This open surgical procedure was performed routinely in years past. However, clinical studies have found a recurrence rate as high as thirty six percent (36%) within about four (4) years. Other existing techniques have demonstrated a lower recurrence rate and have been adopted as better long-term solutions.

Saphenous vein stripping was most often used prior to the advent of the endovenous ablation techniques largely used today. The advantages of vein stripping over high-ligation were related to the ligation being performed at one location near the saphenofemoral junction. During the procedure, the saphenous vein is exposed through a short proximal incision and the vein is simply ligated to close off its lumen to prevent blood flow through it. The high recurrence rate oftentimes is due to incompetent proximal valves in the tributary veins that drain into the long saphenous vein distal to the high ligation point. Over time, these veins can develop valvular incompetence leading to the same or worse symptoms than before the high-ligation procedure. By removing the saphenous vein in the thigh through stripping, recurrence is less likely.

The apparatus and methods described herein may combine one or more of the advantages of the various techniques described above and minimize disadvantages by enabling a percutaneous approach that requires only a minimal amount of local anesthesia. For example, the saphenous vein may be segmentally closed at one or more locations in the region of the thigh, e.g., at the groin, mid-thigh, and distal thigh, so that the disadvantage of the high-ligation procedure, namely a high recurrence rate, may be avoided. The percutaneous nature of the apparatus and methods herein may have advantages over vein stripping procedures, e.g., because of their less invasive nature. In addition, the tissue destruction caused by endovenous ablation with radiofrequency or laser energy along the full length of the treated segment of the saphenous vein is also avoided.

In accordance with one embodiment, an apparatus for closing a tubular structure is provided that includes one or more of the following components:

1) an ultrasound imaging machine with an external probe, which may be placed on the patient's skin directly over or very close to a desired treatment site. A needle guide may be attached to the ultrasound probe to enable controlled insertion of a needle tip through the saphenous vein under direct visual control;

2) a clip including shape memory metal and proximal and distal tines or extensions, which may be deployed to compress against the outer wall of the vein, closing it off;

3) a clip that is preloaded in a needle deployment apparatus;

4) a needle deployment apparatus including a needle having an oval shaped, rectangular, or other oblong lumen or slot within which a clip may reside such that the clip may be deployed through a distal end of the needle;

5) a needle hub having one or more markings, which may enable directional control of the clip before and during deployment;

6) a pusher component, e.g., within the needle slot, e.g., having an oval shaped, rectangular, or other oblong cross-section, e.g., similar to the needle lumen or slot;

7) a spacer or "stop" initially located between a proximal hub of the needle and a proximal end of the pusher component, e.g., to enable sequential deployment of one or more clips;

8) a track to control or limit movement of the pusher member and needle to allow multiple stages of deployment of the clip;

9) an outlet port adjacent a distal tip of the needle and a source of fluid communicating with the outlet port to deliver fluid, e.g., epinephrine, around a vessel being occluded; and 10) an electrocautery needle including one or more electrodes coupled to an electrical energy source to deliver electrical energy before, during, or after deployment of a clip from the needle to enhance occlusion of a vessel.

In accordance with another embodiment, a method for closing a tubular structure within a patient's body is provided that includes the following sequence of steps (in this sequential order or other order, optionally with some steps omitted, as desired):

1) a target vein may be imaged, e.g., with ultrasound, and a location for vein closure may be identified;

2) the patient's skin may be marked above site(s) of planned closure;

3) the skin may be prepped and/or anesthetized at the planned puncture site(s);

4) the vein may be imaged in cross-sectional and/or longitudinal view, e.g., using ultrasound;

5) a tip of a delivery needle may be passed into-and-through the vein, e.g., using an ultrasound transducer with a needle guide or otherwise using ultrasound visual control;

6) fluid may be injected around the vein, e.g., via the delivery needle. In an exemplary embodiment, the fluid may include epinephrine and/or other compound, e.g., to induce vasospasm and/or cause the vein to contract around the needle after it has pierced the vein, e.g., to create a smaller target for closure;

7) the tip of the needle may be positioned posterior to the inner wall of the vein, e.g., one or two millimeters (1-2 mm) deep beyond the inner wall of the vein;

8) the orientation of an occlusion clip carried within the needle may be checked, e.g., using one or more markers on a proximal hub of the needle, e.g., to align the marker substantially parallel to a longitudinal axis of the vein and/or align tines of the occlusion clip substantially perpendicular to the longitudinal axis of the vein;

9) the occlusion clip may be deployed from a distal end of the needle, e.g., using a pusher member within the needle, such that the occlusion clip closes around the vein; for example, a distal portion of the clip, e.g., distal tines or extensions, may initially be deployed by advancing the pusher member;

10) a "stop" may then be removed while the needle is held substantially stationary, e.g., with the distal tip held steadily in place relative to the vein;

11) the needle may be withdrawn while the pusher member remains substantially stationary to deploy a central portion of the occlusion clip and then a proximal portion, e.g., proximal tines or extensions;

12) the needle and pusher member may be removed, leaving the occlusion clip in place, e.g., surrounding, capturing and/or otherwise closing the vein at the closure site;

13) closure of the vein may be checked, e.g., using ultrasound imaging and/or Doppler evaluation, to ensure occlusion of vein; the process, e.g., steps 1) to 12) may be repeated, if desired, at one or more additional closure sites;

14) a dressing may be applied at the puncture site(s); and 15) a compression garment may be placed on the patient's leg, e.g., over the dressing and/or otherwise over the puncture site(s).

One or more occlusion clips may be used at a single location or multiple locations to effectively close the vein of interest.

In accordance with yet another embodiment, an apparatus is provided for closing a tubular structure within a patient's body that includes a needle or other tubular member comprising a proximal end including a hub, a distal end including a sharpened distal tip, a lumen having an oblong cross-section extending proximally from the distal end, and defining a longitudinal axis between the proximal and distal ends; a clip compressible between a relaxed state in which a plurality of tines of the clip are shaped to engage and close a tubular structure within a patient's body, and a stressed state in which the tines are compressed to allow the clip to be loaded into the lumen in a predetermined orientation about the longitudinal axis. The apparatus may also include a pusher member comprising a proximal end and a distal end sized for advancement within the lumen for deploying the clip from the distal tip of the needle such that the tines engage and close a tubular structure through which the tubular member is directed.

In an exemplary embodiment, the plurality of tines of the clip include a pair of distal tines extending from a first end of a central region of the clip and a pair of proximal tines extend from a second end of the central region. The distal tines, proximal tines, and the central region may define a plane in the relaxed configuration, and the distal and proximal tines may remain substantially within the plane when the tines are compressed into the stressed state, or may extend out of the plane when the tines are compressed into the stressed state.

In another exemplary embodiment, the distal tines may have substantially the same length as the proximal tines. Alternatively, the distal tines may be substantially shorter than the proximal tines.

In yet another exemplary embodiments, the distal tines may extend from the central region to define opposing hook shapes in the relaxed state and the proximal tines may extend from the central region such that the tines at least partially surround the central region and the distal tines within the plane in the relaxed state. In this embodiment, the proximal tines may be substantially straightened such that the proximal tines are axially aligned with the central region in the stressed state and/or the distal tines may be substantially straightened such that the distal tines are axially aligned with the central region in the stressed state.

Optionally, the clip may include an eyelet or other aperture for receiving a wire or other filament, e.g., to facilitate loading the clip into the lumen of the tubular device.

In addition or alternatively, the apparatus may include a source of fluid communicating with a outlet in the distal tip to deliver fluid, e.g., including epinephrine, into tissue adjacent or around the target tubular structure. For example, the source of fluid may be coupled to a port on the hub for delivering the fluid through the lumen around the clip and out the distal tip. Alternatively, the port on the hub may communicated with a separate infusion lumen and the distal tip may include one or more outlet ports for delivering the fluid adjacent the distal tip.

In accordance with still another embodiment, an apparatus is provided for closing a tubular structure within a patient's body that includes a tubular member comprising a proximal end including a hub, a distal end including a sharpened distal tip such that the tubular member may be directed into-and-through a tubular structure within a patient's body, a lumen extending between the proximal and distal ends, and defining a longitudinal axis between the proximal and distal ends; and a clip comprising a proximal set of tines or extensions and a distal set of tines or extensions, the clip compressible between a relaxed state in which the tines or extensions are shaped to engage and close a tubular structure within a patient's body, and a stressed state in which the tines or extensions are compressed to allow the clip to be loaded into the lumen in a predetermined orientation about the longitudinal axis. The apparatus may also include a pusher member comprising a proximal end and a distal end sized for advancement within the lumen for deploying the clip from the distal tip of the tubular member such that the distal tines or extensions are deployed initially to partially engage a tubular structure and the proximal tines or extensions are deployed subsequently to further engage the tubular structure, the clip resiliently returning towards the relaxed state to substantially close the tubular structure through which the tubular member is directed.

In accordance with yet another embodiment, a method is provided for closing a tubular structure within a patient's body, e.g., a vein, that includes inserting a distal tip of a delivery device into the patient's body into-and-through the tubular structure, the delivery device carrying a clip including a set of distal tines and a set of proximal tines in a stressed state; partially deploying the clip such that a set of distal tines of the clip extend from the distal tip beyond the tubular structure and elastically deform towards a relaxed state; partially withdrawing the delivery device to engage the tubular structure with the distal tines; and fully deploying the clip such that a set of proximal tines are released from the distal tip and elastically deform towards a relaxed state, thereby occluding the tubular structure.

Optionally, fluid may be injected adjacent and/or around the tubular structure, e.g., via the delivery device, to cause the tubular structure to contract around the distal tip. In an exemplary embodiment, the fluid may include epinephrine, e.g., to induce smooth muscle contraction and/or induce vasospasm in the tubular structure, which may facilitate capturing, engaging, compressing, and/or otherwise occluding the tubular structure.

In another embodiment, electrical energy may be delivered to the tubular structure, e.g., via one or more electrodes on or adjacent the distal tip of the delivery device to cauterize and/or cause contraction of the tubular structure.

In yet another embodiment, an ultrasound transducer may be placed against the patient's skin above the tubular structure, and the delivery device may be inserted into the skin through a needle guide coupled to the transducer. Optionally, the needle guide may include a vibrator to vibrate a shaft of the delivery device, e.g., to enhance imaging using the transducer.

The following is a list of one or more advantages that may be achieved using the apparatus and methods described herein, e.g., as compared to endovenous laser, radiofrequency ablation technologies, and other methods that destroy the vein by applying chemicals or applying other forms of energy along the full length of the inside of the vein:

1) No open surgery is involved;
2) There is no need for a laser or radio frequency generator or console;
3) There is no burning of the vein or boiling of blood;
4) No tumescent anesthesia is required;
5) The procedure may be faster than radio frequency ablation or laser;
6) There is little risk of systemic embolization of sclerotherapy agent;
7) The risk of recanalization of the vein is lower than with ablation procedures;
8) The procedure may be less painful than laser or radio frequency ablation;
9) The procedure may be less expensive than laser or radio frequency ablation; and
10) Post-procedural inflammation may be minimized as trauma is isolated to the site(s) of closure instead of affecting the full length of the vein, e.g., as in the case of laser or radio frequency ablation.

Other aspects and features of the present invention will become apparent from consideration of the following description taken in conjunction with the accompanying drawings.

BRIEF DESCRIPTION OF THE DRAWINGS

The invention will be better understood by reference to the Figures of the drawings wherein:

FIGS. 5A-5E are cross-sectional views of a patient's body, showing an exemplary method for closing a blood vessel using the apparatus of FIG. 1.

FIGS. 7A and 7B are perspective and front views, respectively, of yet another embodiment of an occlusion clip.

DETAILED DESCRIPTION OF THE EXEMPLARY EMBODIMENTS

Figure 1:
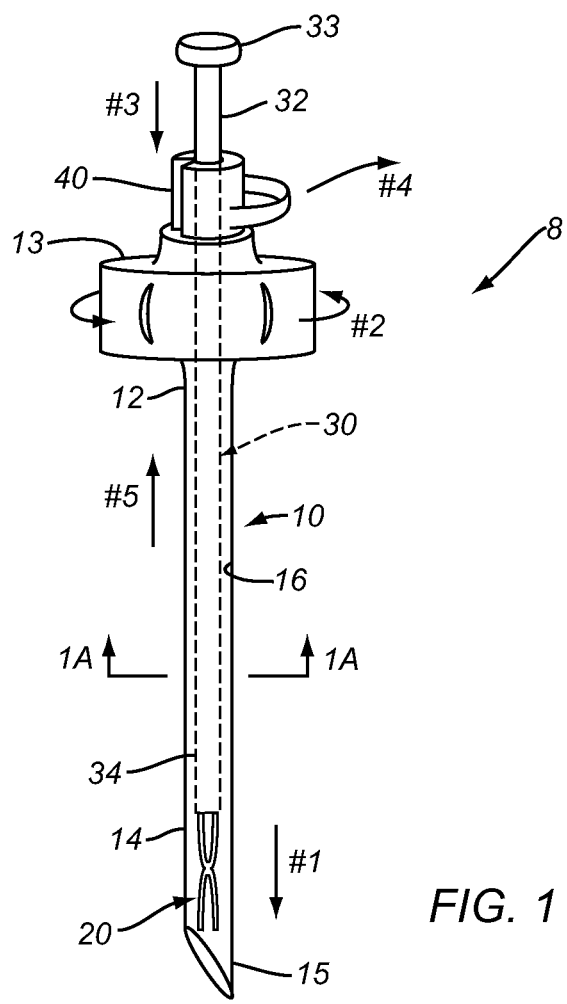
FIG. 1 is a perspective view of an exemplary embodiment of an apparatus for delivering an occlusion clip from a needle.

Turning to the drawings, FIG. 1 shows an exemplary embodiment of an apparatus 8 for delivering a clip 20 into a patient's body, e.g., to close a tubular structure, such as a saphenous vein or other blood vessel. Generally, the apparatus 8 includes a needle or other tubular member 10, one or more clips 20, and a pusher member 30. Optionally, the apparatus 8 may be part of a system, e.g., including an ultrasound transducer and/or other imaging device, a needle guide, and the like (not shown).

The needle 10 generally includes a proximal end 12 with a hub 50, a distal end 14, and a lumen or slot 16 extending between the proximal and distal ends 12, 14, thereby defining a longitudinal axis 18. One or more clips 20 may be loaded within the lumen 16, and the pusher member 30 may be disposed at least partially within the lumen 16. The distal end 14 of the needle 10 may terminate in a beveled, pointed, or other sharpened distal tip 15, e.g., to facilitate percutaneous introduction of the needle 10 directly through tissue to a target location within a patient's body, as described further below.

Figure 1A:
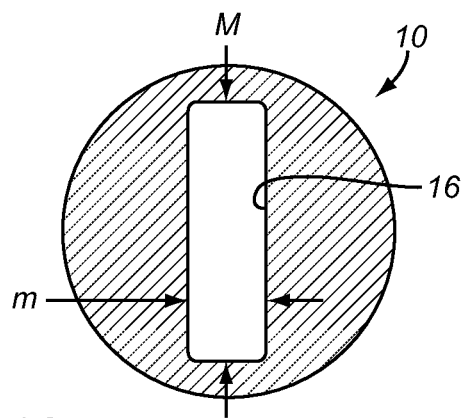
FIG. 1A is an exemplary cross-sectional view of a needle of the apparatus of FIG. 1, taken along line 1A-1A.

As shown in FIG. 1A, the lumen 16 may have an oval shape, a rectangular shape, or other oblong shape, e.g., including a major axis "M" and a smaller minor axis "m," e.g., such that the clip(s) 20 may be loaded into the lumen 16 in a predetermined rotational orientation about the longitudinal axis 18 of the needle 10. As used herein, "oblong" refers to any cross-sectional shape that includes a major axis that is larger than a minor axis and is configured to slidably receive one or more clips 20 therein while constraining the clip(s) 20 in a stressed configuration, as described further below.

Figure 9:
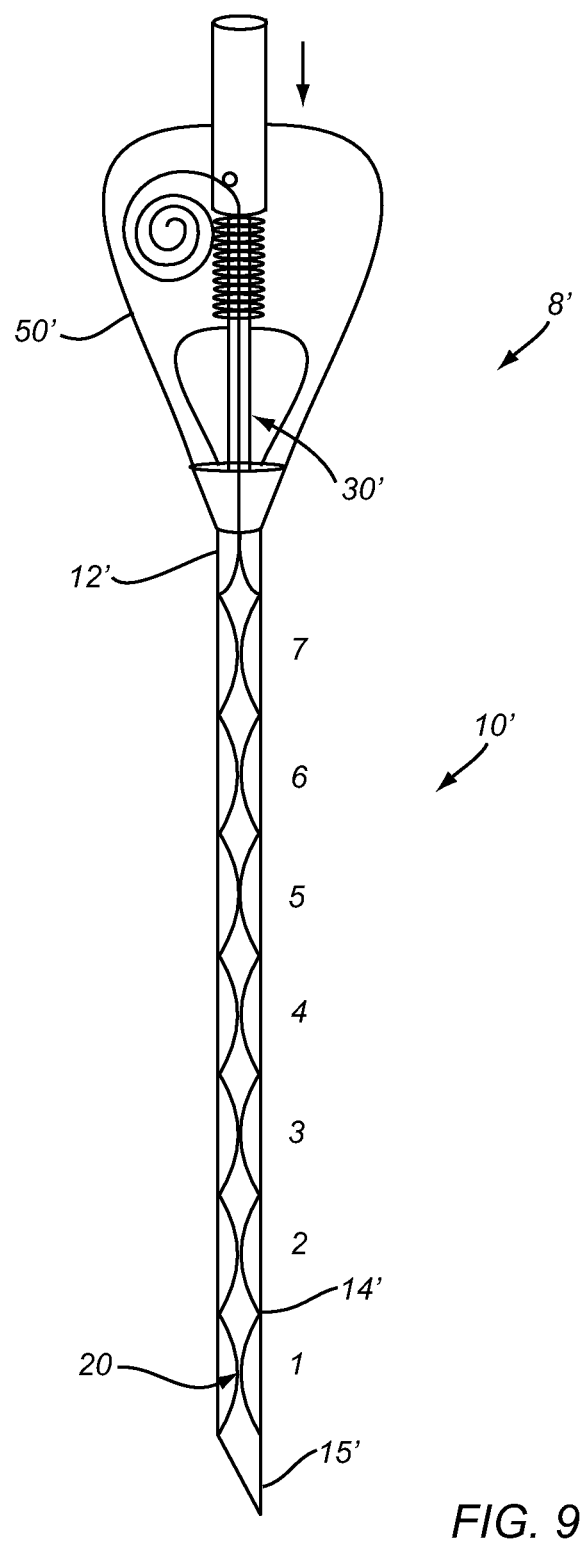
FIG. 9 is a perspective view of another exemplary embodiment of an apparatus for delivering occlusion clips.

In the embodiment shown in FIG. 1, a single clip 20 (which may be any of the embodiments shown and described herein) is provided within the lumen 16. Alternatively, as shown in FIG. 9, a needle 10' may be provided that includes a plurality of clips 20 within the lumen 16,' e.g., spaced apart axially from one another, such that multiple clips 20 may be deployed sequentially from the needle 16.' Otherwise, the needle 10' may be constructed similar to the needle 10 (like elements labeled similarly, except with a "'") and/or other embodiments herein.

Figure 2A:
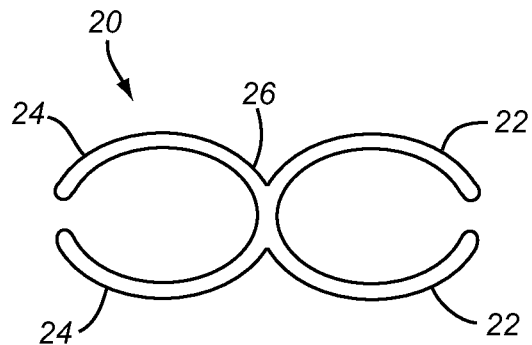
FIGS. 2A-2C are side views of exemplary embodiments of an occlusion clip that may be delivered using the apparatus of FIG. 1.

Turning to FIG. 2A, the clip(s) 20 generally includes one or more tines or extensions 22, 24 thereon for engaging tissue, e.g., a wall of a vein or other tubular structure within a patient's body. For example, as shown, the clip 20 may include a distal set of tines 22 and a proximal set of tines 24, e.g., extending in opposite directions from a central region 26 of the clip 20. As shown, the clip 20 may generally define a plane, i.e., wherein the tines 22, 24 and central region 26 all lie within the same plane, e.g., perpendicular to the thickness of the clip 20.

Figure 2B:
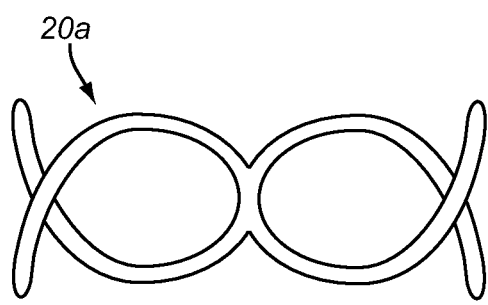
Figure 2C:
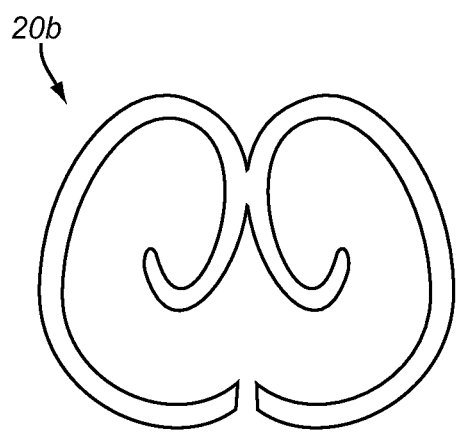
Figure 3A:
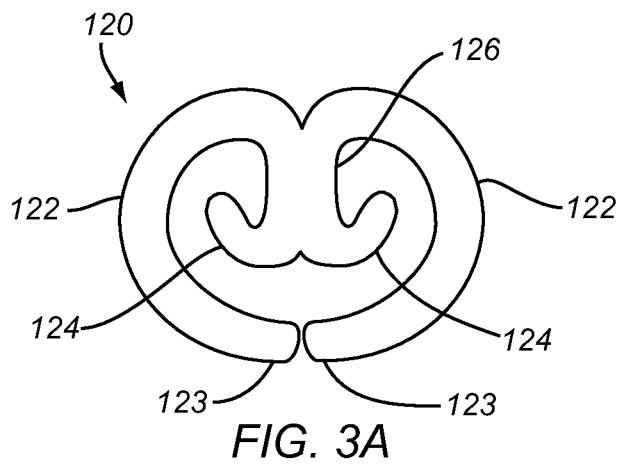
FIGS. 3A-3C are front views of additional embodiments of occlusion clips that may be used in the apparatus and methods herein.

The tines 22, 24 may be biased to a curved or other shape, e.g., a partial loop defined by each set of opposing tines 22, 24 within the plane, such that tips 23, 25 of the respective sets of tines 22, 24 (including one distal tine 22 and one opposing proximal tine 24) are located adjacent one another and are spaced apart as shown in FIG. 3A. Alternatively, as shown in FIG. 2B, a clip 20' may be provided in which each set of tines 22,' 24' overlap (thereby extending slightly out of the plane, e.g., at the tips 23,' 25'), or as shown in FIG. 2C, a clip 20" may be provided in which the tips 23," 25" of each set of tines 22," 24" contact one another. In any of the embodiments herein, the tips 23, 25 of the tines or extensions 22, 24 may be sharpened, beveled, barbed, or otherwise configured to facilitate introduction through tissue and/or engagement with the wall of the tubular structure being closed, or may have rounded, bulbous, or other atraumatic shapes, e.g., to allow engagement without penetrating or tearing tissue.

In the embodiment of FIG. 2A, each opposing set of tines 22,24 of the clip 20 defines a generally "C" shape in a relaxed state. In addition, as shown, the distal tines 22 and the proximal tines 24 have the same length, curvature, and/or other similar geometric shapes. However, in alternative embodiments, the pairs of tines 22, 24 may have different shapes and/or lengths than one another.

For example, as shown in FIG. 3A, a clip 120 is shown that includes a substantially straight central region 126, and a pair of distal tines 122 that extend from a first end of the central region 126 to define "J" or hook shapes. A pair of proximal tines 124 extend from a second end of the central region 126 to define a generally "C" shape that at least partially surrounds the central region and the distal tines 122 within a single plane. Thus, in this embodiment, the distal tines 122 may be relatively short and the proximal tines 124 may be relatively long, but with the tines of each pair (i.e., both distal tines 122 and both proximal tines 124) having substantially the same length and substantially similar shapes. In the embodiment shown in FIG. 3A, the proximal tines 124 may have sufficient length that the tips 125 thereof touch or are disposed adjacent but slightly separate from one another.

Figure 3B:
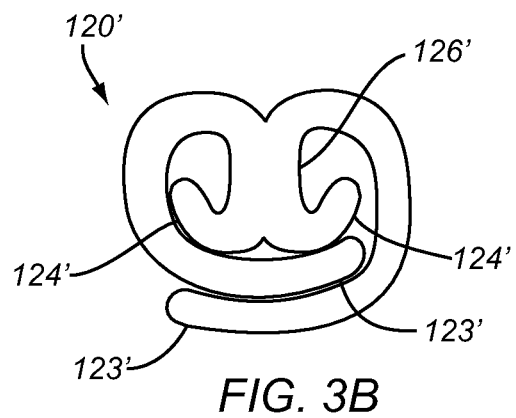
Figure 3C:
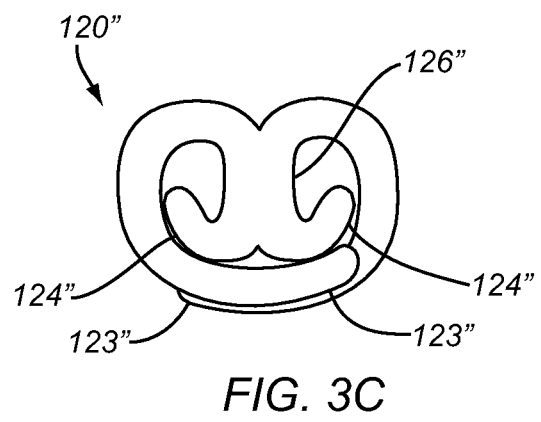

Alternatively, as shown in FIG. 3B, the clip 120' may include proximal tines 124' that together are substantially longer than the periphery of the central region 126' and distal tines 122' such that the tines 124' overlap one another within the plane, e.g., with the tip 125' of one tine 124' closer to the central region 126' than the other tip 125.' In a further alternative, as shown in FIG. 3C, the clip 120" may include proximal tines 124" that surround the central region 126" and distal tines 122" such that the tips 125" overlap outside the plane.

With reference to the clip 122 of FIG. 3A (but generally applicable to the other clips herein), in exemplary embodiments, the central region 126 may have a length between about one and four millimeters (1-4 mm), the distal tines 122 may have a length between about two and eight millimeters (2-8 mm), and the proximal tines 124 may have a length between about four and twelve millimeters (4-12 mm). For example, the proximal tines 124 may have sufficient length to at least partially or entirely surround the outer wall of a vessel being occluded, e.g., a vein having a diameter between about four and fifteen millimeters (4-15 mm).

Returning to FIG. 2A (but applicable to other the clips herein), the clip 20 may be formed from an elastic or superelastic material, e.g., such that the tines 22, 24 may be compressed to facilitate loading the clip(s) 20 into the needle 10 and resiliently expandable to surround, penetrate, and/or otherwise engage a wall of a tubular structure and/or surrounding tissue to close the tubular structure. Alternatively, the clip(s) 20 may be formed from shape memory material, e.g., that may be loaded into the needle 10 in a first state, e.g., a martensitic state at a first temperature below body temperature, and may be deployable from the needle 10 in a second state, e.g., an austenitic state at body temperature in which the clip(s) 20 may remember an engagement shape for closing the tubular structure.

Figure 4A:
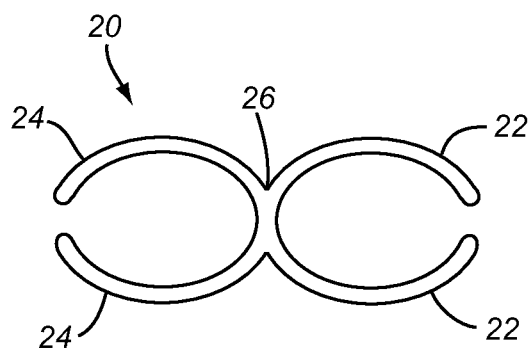
FIGS. 4A-4C show an exemplary method for compressing the occlusion clip of FIG. 2A from a relaxed or expanded state (FIG. 4A) to a compressed state for loading into a delivery device (FIG. 4C), such as the apparatus of FIG. 1.
Figure 4B:
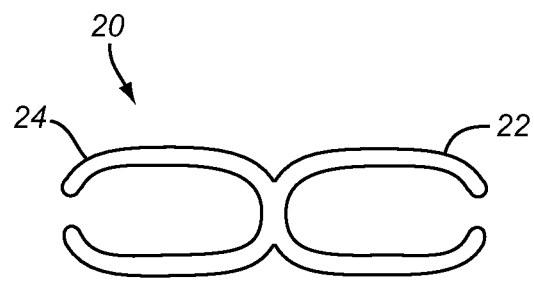
Figure 4C:
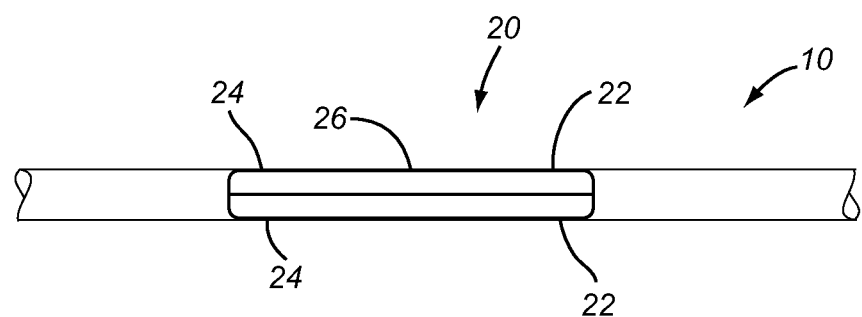

For example, as shown in FIGS. 4A-4C, a method is shown for compressing the clip 20 of FIG. 2A, e.g., to allow loading into a delivery device, such as the lumen 16 of the needle 10 shown in FIG. 1. Initially, the clip 20 may be formed and provided in a relaxed state (e.g., as shown in FIG. 4A) wherein the pairs of tines 22, 24 curve to an open configuration. The distal pair of tines 22 may be compressed together and the proximal pair of tines 24 may be compressed together, e.g., as shown in FIG. 4B, until the tines 22, 24 are pressed adjacent one another in a substantially linear configuration aligned with the central region 26 to define a compressed or stressed state, as shown in FIG. 4C. In the substantially linear configuration or compressed state, the clip 20 may be loaded into the lumen 16 of the needle 10 with the distal tines 22 closer to the distal tip 15 than the proximal tines 24, as described elsewhere herein.

The thickness of the clip 20 may be slightly less than the minor dimension "m" of the lumen 16, and the width of the tines 22, 24 within the plane may be slightly less than the major axis "M." Given the relative dimensions, the clip 20 may be slidably received in the lumen 16 with the tines 22, 24 maintained in the substantially linear configuration by the walls of the lumen 16. Optionally, the lumen 16 may provide sufficient clearance around the clip 20 to allow fluid to be delivered through the lumen 16 with the clip 20, or the lumen 16 include a longitudinal groove (not shown), e.g., in a wall of the major dimension to provide a path for fluid to travel through the lumen 16.

Alternatively, in the embodiment shown in FIG. 3A, the proximal tines 124 may be unwrapped from around the central portion 126 and substantially straightened within the plane, e.g., such that the proximal tines 124 are aligned axially with the central region 126. The distal tines 122 may then be substantially straightened opposite the proximal tines 124, e.g., such that the distal tines 122 are aligned axially with the central region 126 and the straightened proximal tines 124. Thus, the clip 120 may be loaded into a needle, e.g., into the lumen 16 of the needle 10 of FIG. 1 in a substantially linear configuration, similar to that shown in FIG. 4C. Similarly, the clips 120,' 120" shown in FIGS. 3B and 3C may be elastically deformed into the substantially straightened configuration and loaded into the lumen 16 of the needle 10.

Returning to FIG. 1, the needle may include a substantially rigid tubular body 10, e.g., a section of hypotube and the like, with the distal end 14 sharpened to a pointed or beveled tip 15. The hub 50 may have a size and/or shape to allow the needle 10 to be held and/or manipulated during use. The hub 50 may be attached to the proximal end 12 of the tubular body 10, e.g., by one or more of bonding with adhesive, sonic welding, interference fit, cooperating connectors (not shown), and the like.

As shown in FIG. 1, the hub 50 may include one or more markers and/or other features 53 located about the periphery of the hub 50, e.g., to provide a visual indication of the orientation of the clip(s) 20 within the lumen 16 of the needle 10. For example, as shown, the hub 50 may have an oblong shape, e.g., such that a major axis of the hub 50 is ninety degrees offset from the major dimension of the lumen 16. In addition or alternatively, one or more colored or other markers or elements (not shown) may be provided on the hub 50, e.g., on opposite sides of the hub 50 aligned with the minor dimension of the lumen 16.

The clip(s) 20 may be loaded into the lumen 16 of the needle 10 such that the opposing pairs of tines or extensions 22, 24 are oriented along the major dimension of the lumen 16. The oblong shape of the hub 50 and/or markers on the hub 50 may identify the relative rotational orientation of the lumen 16, thereby indicating the plane or direction in which the tines 22, 24 will expand as the clip 20 is deployed from the needle 10, as described further elsewhere herein.

With continued reference to FIG. 1, the pusher member 30 includes a proximal end 32, e.g., including a plunger stem 33, and a distal end 34 disposed within the needle lumen 16 adjacent the clip(s) 20. At least the distal end 34 of the pusher member 30 has an oblong cross-section, e.g., having major and minor dimensions similar to and/or smaller than the lumen 16, such that at least the distal end 34 of the pusher member 30 is slidable axially relative to the needle 10, e.g., between a proximal or first position, as shown in FIG. 1, and one or more distal positions, e.g., second and third positions, as described further below.

For example, as shown in FIG. 1, the apparatus 8 may include a removable stop 40, e.g., disposed around the proximal end 32 of the pusher member 30, e.g., adjacent the hub 50. The stop 40 may be a "C" shaped collar or other element that extends at least partially around the pusher member 30 and has a predetermined length to limit advancement of the pusher member 30. In the proximal or first position shown in FIG. 1, the clip 20 may be disposed entirely within the lumen 16, e.g., such that distal tines 22 of the clip 20 are disposed within and/or adjacent the distal tip 15 of the needle 10.

The pusher member 30 may be advanceable to a second or distal position, e.g., to deploy the distal tines 22 of the clip 20 from the lumen 16 beyond the distal tip 15 while the proximal tines 24 remain within the lumen 16. For example, the pusher member 30 may be advanced until the plunger stem 33 on the pusher member 30 abuts the stop 40, thereby preventing further advancement of the pusher member 30. The length of the stop 40 may correspond to deploying a distal portion of the clip 20, e.g., the distal tines 22 beyond the distal tip 15, such that the distal tines 22 resiliently return at least partially towards the relaxed state.

The stop 40 may be removable from around the pusher member 30, whereupon the needle 10 may be retracted proximally, e.g., equivalent to advancing the pusher member 30, until the pusher member 30 is in a third position relative to the needle 10, e.g., in which the entire clip 20 is deployed from the lumen 16 beyond the distal tip 15 of the needle 10. As the proximal tines 24 are deployed from the lumen 16, they may also resiliently return towards the relaxed state, thereby surrounding or otherwise engaging the tubular structure to be closed.

Alternatively, the hub 50 and/or pusher member 30 may include a cooperating track (not shown) instead of the stop 40 to control or limit movement of the pusher member 30 relative to the needle 10. For example, the track may include a first axial section allowing the pusher member 30 to be advanced axially from the first position to the second position, thereby partially deploying the clip 20, e.g., the distal tines 22. When desired to fully deploy the clip 20, the pusher member 30 may then be partially rotated, e.g., to move the pusher member 30 along a circumference (non-axial) section of the track, and then advanced axially along a third axial section to direct the pusher member 30 and needle 10 from the second position to the third position. Optionally, in this alternative, the hub 50 and/or pusher member 30 may include one or more markers (not shown) that may provide visual confirmation when the pusher member 30 is properly aligned along the track, e.g., sufficiently rotated to allow movement between the second and third positions.

With additional reference to FIGS. 5A-5E, the steps of an exemplary method for using the apparatus 8 are labeled 1 through 5 of FIG. 1:

Initially, a location 92 along a vein or other body lumen 90 may be identified as a target location for delivering a clip 20, e.g., a saphenous vein experiencing valvular incompetence and the like. Optionally, a mark (not shown) may be applied to the patient's skin above the target location, e.g., to identify a point of entry for the needle 10. A local anesthetic may be injected or otherwise delivered to the skin and/or underlying tissue, e.g., between the skin and vein and/or around the vein, optionally, using the needle 10, as described elsewhere herein.

As labeled in step #1, the needle 10 may be inserted through the skin and the point of entry and passed into-and-through the vein 90, e.g., using ultrasound visual control, as shown in FIG. 5A. The distal tip 15 of the needle 19 may be positioned beyond the posterior or inner wall 94 of the vein 90, e.g., about one or two millimeters (1-2 mm) deep beyond the posterior wall 92 of the vein 90.

Optionally, fluid may be delivered through the needle 10, e.g., through the lumen 16 and out the distal tip 15, into the region adjacent the vein 90. As described elsewhere herein, the lumen 16 may be sized to accommodate injecting fluid around the clip(s) 20 therein and through the outlet of the distal tip 15. Alternatively, the needle 10 may include a separate lumen (not shown) communicating between the hub 50 and a side port (not shown) adjacent the distal tip 15.

Figure 12A:
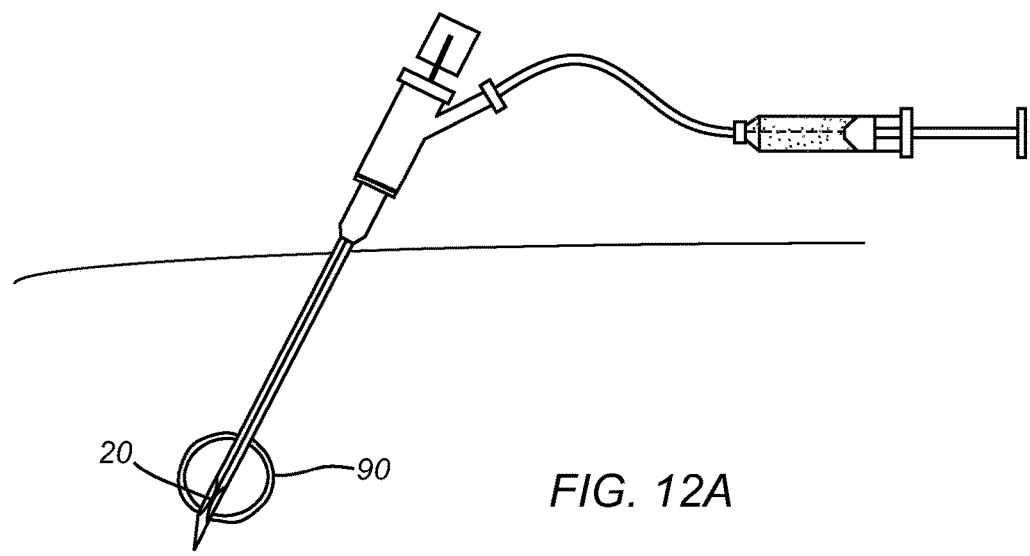
FIGS. 12A and 12B are side views of another exemplary embodiment of an apparatus for delivering one or more occlusion clips, including a side port, outlet port, and a source of fluid for delivering the fluid via the outlet port around a vessel being occluded.
Figure 12B:
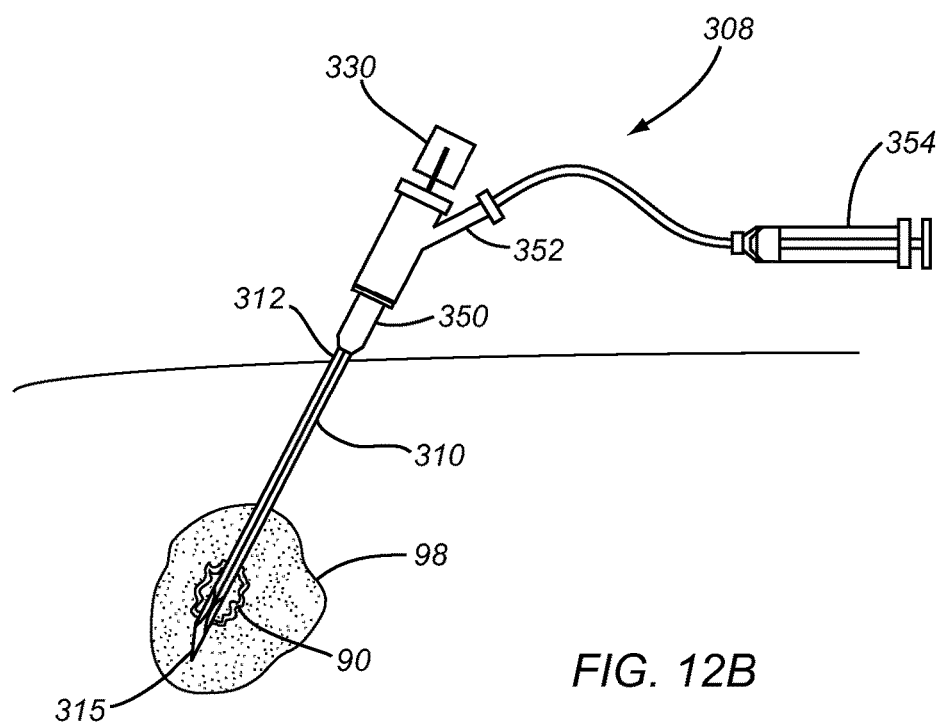

An exemplary embodiment of such a needle 310 is shown in FIGS. 12A and 12B in which the needle 310 includes a hub 350 with a side port 352, e.g., including a luer fitting and the like (also not shown) for connecting a source of fluid 354 to the hub 350. The side port 352 may communicate with the clip lumen or a dedicated fluid lumen (not shown), e.g., extending to the distal tip 315 or a separate outlet port (not shown) adjacent the distal tip 315. Alternatively, a side port adapter including a side port (not shown) may be coupled over the proximal end 312 of the needle 310, and the pusher member 330 may be loaded into a passage through the side port adapter (also not shown) until the distal end 34 is received within the lumen 16.

The source of fluid 354 may include an anesthetic, e.g., that may be injected into the patient's skin (not shown) during introduction of the needle 310, or into tissue adjacent or around the vessel 90 being occluded. In an exemplary embodiment, the fluid may include epinephrine, which may be injected around the vein 90 to induce small muscle contraction or vasospasm, e.g., causing the vein 90 to contract around the needle 10 after being pierced through the vein 90. For example, a ten to twenty milliliter (10-20 mL) bolus 98 (as shown in FIGS. 12A and 12B) of an anesthetic solution of one percent Lidocaine, and epinephrine in 1:100,000 concentration may be injected. If the vein 90 is contracted, it may provide a smaller target for the clip 20 to occlude, e.g., facilitating tines of the clip 20 surrounding, compressing, and/or otherwise engaging the wall of the vein 90. The fluid may also create a volume around the vein 90, e.g., directing other tissue away from the outer wall of the vein 90 or otherwise reducing friction or other resistance, which may facilitate deployment of the clip 20 around the vein 90.

Returning to FIG. 1, the orientation of the occlusion clip 20 may be checked, e.g., using one or more markers on the needle hub 50. For example, the needle 10 may be rotated about its longitudinal axis such that the wider dimension of the oblong hub 50 and/or the marker(s) on the hub 50 are aligned substantially parallel to the longitudinal axis 96 of the vein 90, e.g. as indicated at step #2. In this orientation, the tines 22, 24 of the occlusion clip 20 may be oriented across the width of the vein 90, e.g., with the plane of the clip 20 substantially perpendicular to the longitudinal axis 96 of the vein 90.

The pusher member 30 may be advanced until the distal tines 22 of the occlusion clip 20 exit the distal tip 15 of the needle 10, e.g., as indicated at step #3 and shown in FIGS. 5A and 5B. For example, the pusher member 30 may be advanced until the plunger stem 33 contacts the stop 40 (or, alternatively, the end of the first section of the track, not shown) in the second position, thereby preventing further advancement of the pusher member 30. As this occurs, the distal tines 22 may exit the distal tip 15 and curve at least partially around the posterior wall 92 of the vein 90, e.g., at least partially surrounding the wall of the vein 90. For example, the distal tines 22 may engage the posterior wall 94 of the vein 90, e.g., to prevent migration of the clip 20 during subsequent deployment and/or may partially close the vein 90.

The stop 40 may then be removed as the needle 10 is held substantially steadily in place, e.g., as indicated at step #4 (or, alternatively, the pusher member 30 may be rotated to align the track with the second section, also not shown). The needle 10 may be withdrawn as the pusher member 30 is held or otherwise remains substantially stationary, thereby moving between the second and third positions, to deploy the central portion 26 and then the proximal tines 24 of the occlusion clip 20, e.g., as indicated at step #5. The proximal tines 24 may surround and/or compress the wall of the vein 90, thereby closing the lumen of the vein 90. The needle 10 may then be removed leaving occlusion clip 20 in place. Optionally, the procedure may be repeated one or more times, e.g., at the same location and/or different locations along the length of the vein 90, to deliver multiple clips (not shown) to close the vein 90.

Figure 6A:
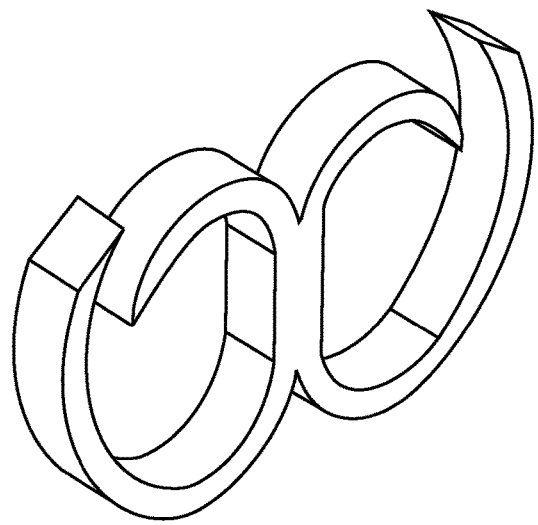
FIGS. 6A and 6B are perspective and front views, respectively, of another embodiment of an occlusion clip.
Figure 6B:
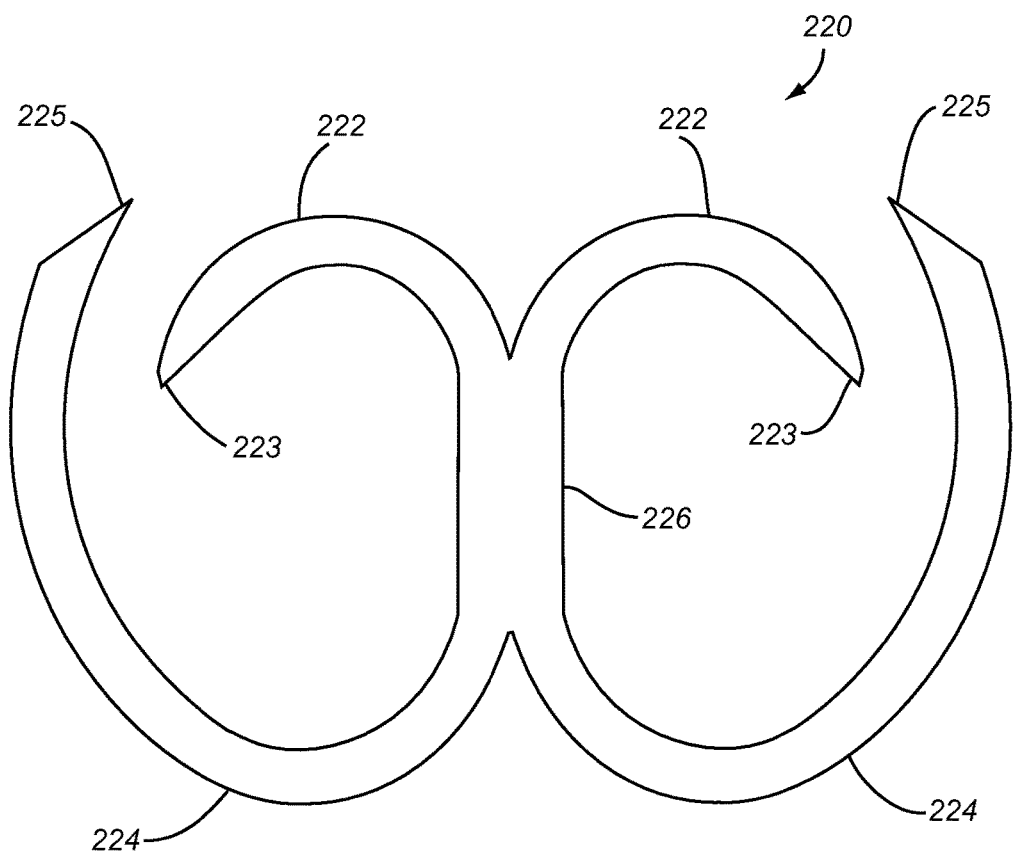

Turning to FIGS. 6A and 6B, another exemplary embodiment of a clip 220 is shown that includes a substantially straight central region 226, a pair of relatively short distal tines 222 that extend from a first end of the central region 226 to define "J" or hook shapes, and a pair of proximal tines 224 that extend from a second end of the central region 226 to define a generally "C" shape that at least partially surrounds the central region and the distal tines 122, e.g., within the same plane. Unlike the clip 120 of FIG. 3A, the tines 222, 224 have sharpened tips 223, 225 rather than atraumatic or rounded tips 123, 125. In an exemplary embodiment, the clip 220 may be formed by one or more of laser cutting, etching, machining, and/or otherwise forming the tines 122, 124 and central region 126 of the clip 220 from a flat sheet, e.g., of Nitinol or other elastic or superelastic material.

Turning to FIGS. 7A and 7B, another exemplary embodiment of a clip 320 is shown that includes a substantially straight central region 326, a pair of relatively short distal tines 322 that extend from a first end of the central region 326, and a pair of proximal tines 324 that extend from a second end of the central region 326. Similar to other embodiments herein, the distal tines 322 may be substantially shorter than the proximal tines 324. The distal tines 322 extend proximally towards the second end of the central region 326 and outwardly away from the central region 326, e.g., to facilitate engaging a posterior wall of a vessel being occluded. The proximal tines 324 may curve outwardly from the second end of the central region 326 back towards the first end of the central region 326, e.g., such that the proximal tines 324 at least partially surround the central region 326 and/or distal tines 322.

Figure 8:
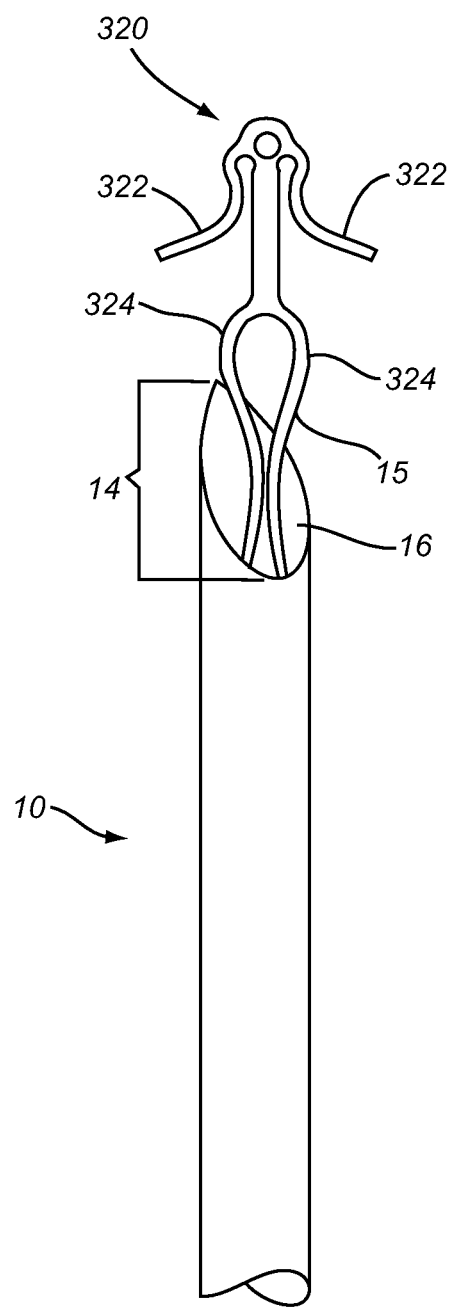
FIG. 8 is a perspective view of the occlusion clip of FIGS. 7A and 7B partially deployed from a delivery device.

In addition, the first end of the central region 326 may include a rounded or other atraumatic tip 327, which may facilitate loading and/or deployment of the clip 320 from a delivery device, such as the needle 10 shown in FIG. 8. For example, the distal tip 327 may facilitate initially deploying the distal tip 327 from the clip 320 from the distal tip 15 of the needle 10, e.g., to prevent snagging of the distal tip 15 on tissue and/or facilitate expansion of the distal tines 322 as they are exposed beyond the posterior wall of the vessel being occluded. As can be seen in FIG. 8, the distal tines 322 may be exposed and resiliently expanded beyond the vessel, whereupon the needle 10 may be partially withdrawn to engage the distal tines 322 around the outer wall of the vessel before deploying the proximal tines 324.

The needle 10 may then be retracted further while maintaining the pusher member (not shown) substantially stationary, whereupon the proximal tines 324 may be deployed from the distal tip 15, thereby releasing the fully deployed clip 320. The proximal tines 324 may then expand around and engage the vessel, e.g., flattening or otherwise compressing the vessel wall inwardly, thereby occluding the vessel similar to other embodiments herein.

Optionally, the clip 320 includes an eyelet or other aperture 328, e.g., in the distal tip 327 of the central region 326. The eyelet 328 may facilitate loading the clip 320 into the needle 10. For example, a wire, thread, or other filament (not shown) may be directed through the eyelet 328 and ends of the filament may be backloaded into the distal tip 15 of the needle 10 and through the lumen 16 (also not shown). The filament ends may be pulled from the proximal end 12 of the needle 10 to draw the clip 320 into the lumen 16, e.g., with the tines 322, 324 being constrained within a sleeve or other mandrel (not shown) to maintain them in the compressed state or substantially linear configuration while being loaded. Once the clip 320 is fully received within the lumen 16, e.g., with the clip distal tip 327 adjacent the needle distal tip 15, the filament may be removed, e.g., by releasing one end and pulling the other distally through the lumen 16, the eyelet 328, and proximally back through the lumen 16.

Figure 10:
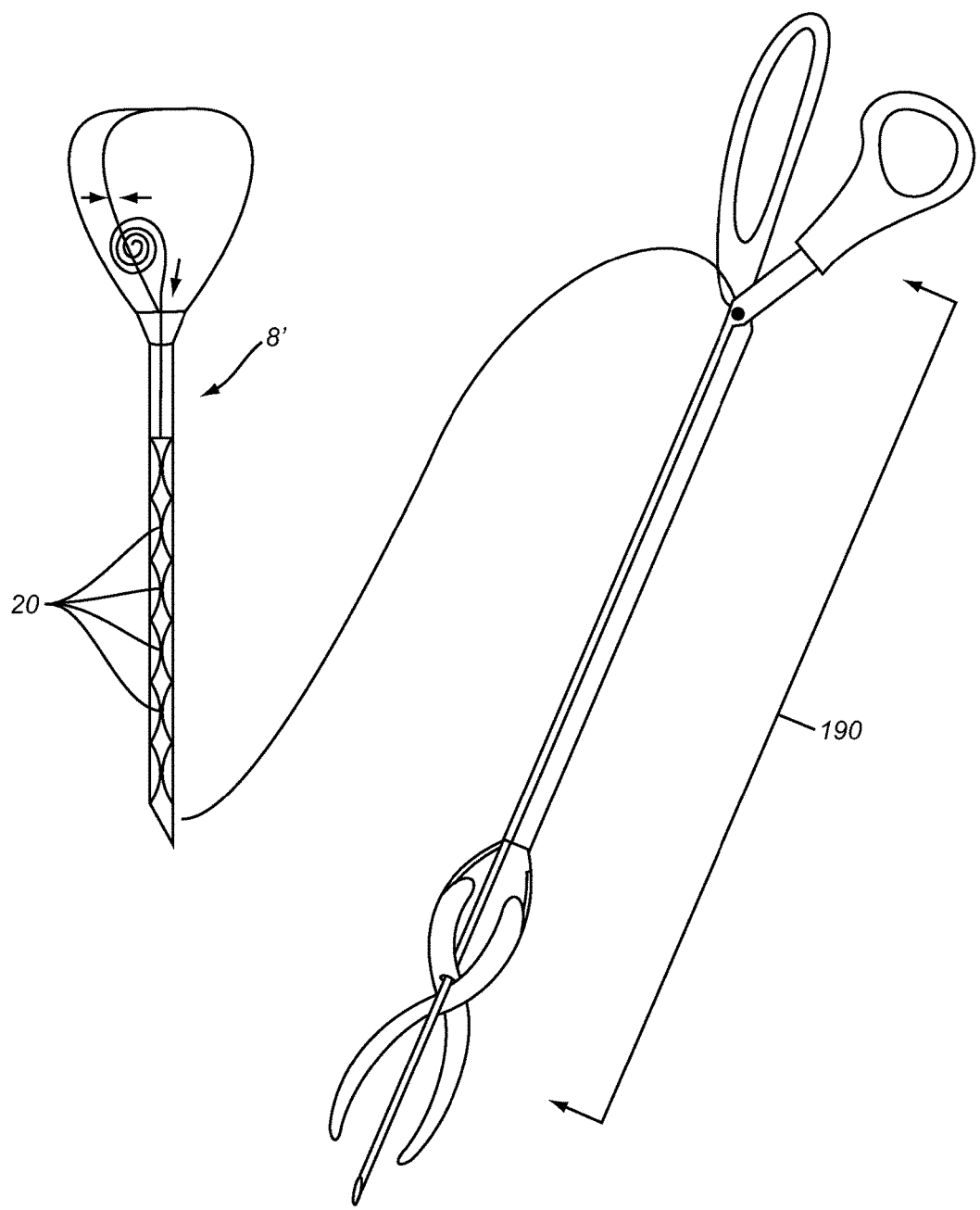
FIG. 10 is a perspective view of an apparatus, similar to that shown in FIG. 9, being loaded into a tool, such as a pair of laparoscopic scissors.

Turning to FIG. 10, another exemplary embodiment of an apparatus 8,' similar to that shown in FIG. 9, is shown being loaded into a tool, such as a pair of laparoscopic scissors 190. The laparoscopic scissors 190 may facilitate introduction of the apparatus 8' and/or delivery of one or more clips 20 in cooperation with the tool 190.

Figure 11:
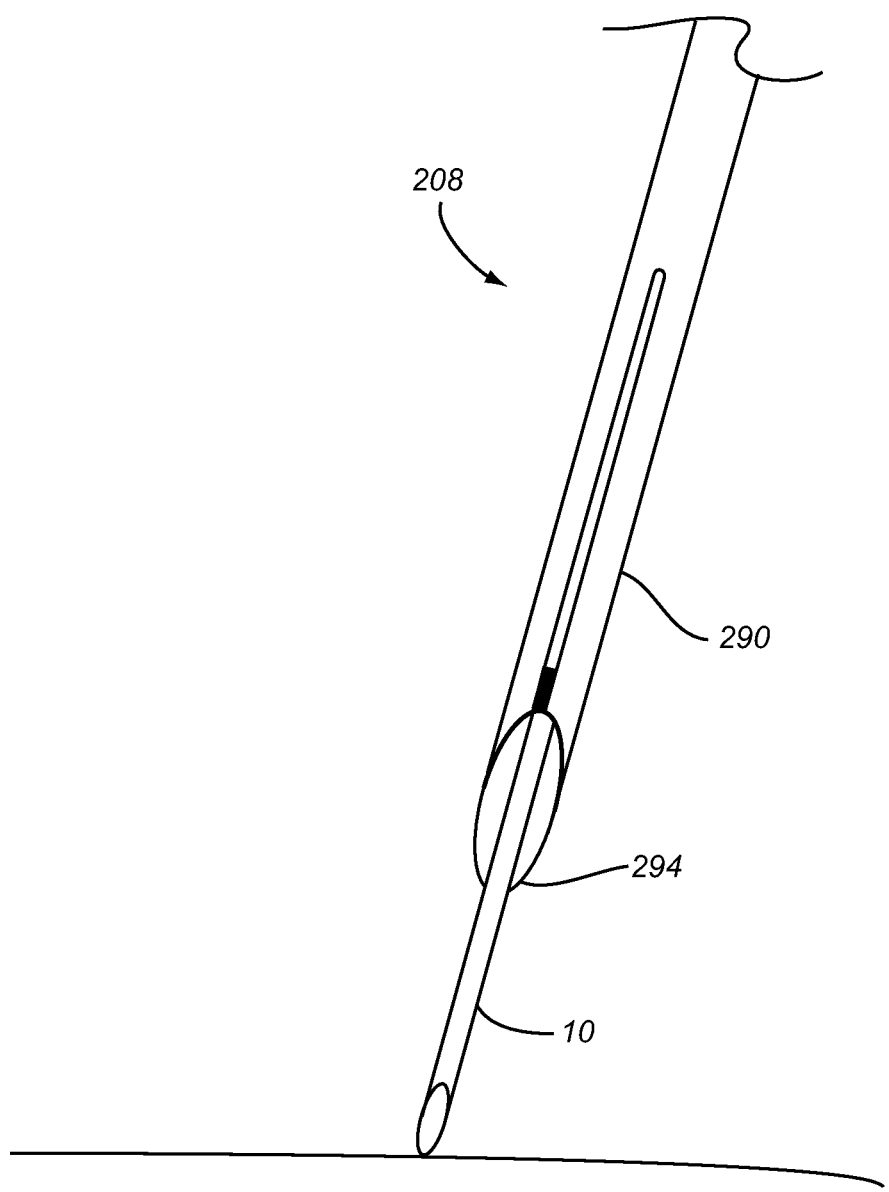
FIG. 11 is a perspective view of a distal portion of a coaxial system including a relatively small needle, e.g., similar to any of the apparatus described herein positioned within a larger needle.

Turning to FIG. 11, yet another exemplary embodiment of a coaxial apparatus or system 208 is shown that includes a relatively small needle 10, e.g., similar to any of the apparatus described elsewhere herein, positioned within a larger needle 290. The larger needle 290 may have a blunt distal end 294, which will not puncture the vein or other vessel being occluded. The system 208 may be inserted through a skin stab incision or percutaneous cannula/port. After the larger outer needle 290 has compressed or flattened the vein, e.g., monitored using external imaging, such as real-time ultrasound imaging, the smaller inner needle 10 may be advanced into-and-through the vein, e.g., through the flattened anterior and posterior walls. Once the smaller needle 10 has traversed the vein, the clip 20 (not shown) may be partially deployed, similar to other embodiments herein. The coaxial system 208 may then be withdrawn (while maintaining an internal pusher member substantially stationary), thereby fully deploying the clip 20. In its fully deployed state, the tines 22, 24 of the clip 20 traverse and close the vein. Depending on the size of the clip and the diameter of the vein, one or more clips may be deployed for complete vein closure at multiple locations along the length of the vein.

Figure 13:
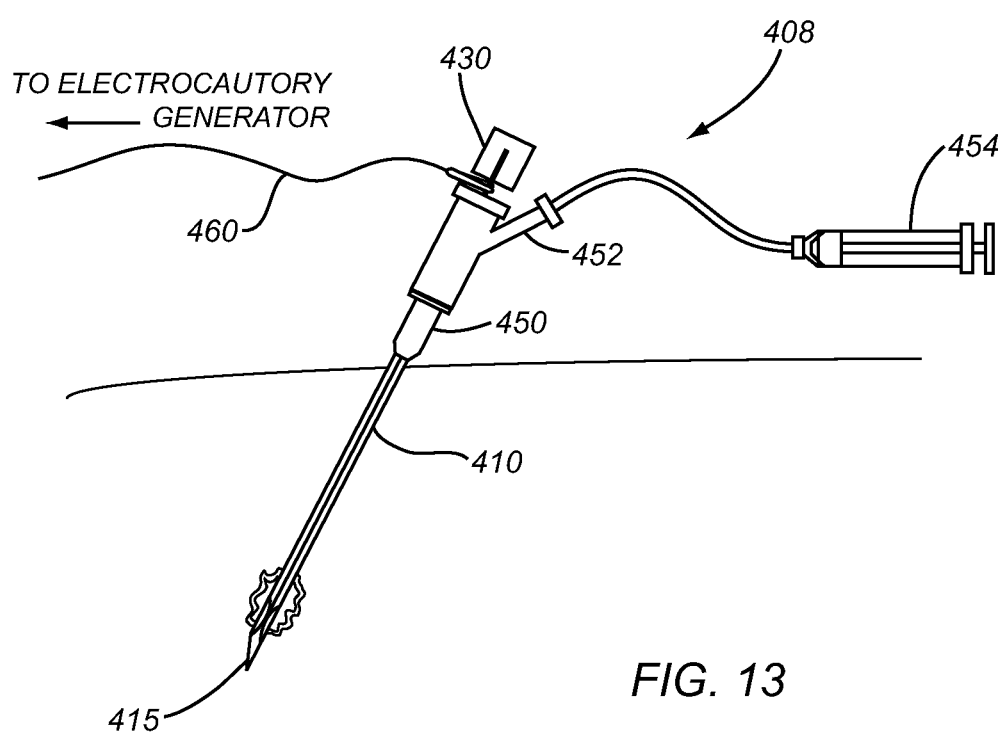
FIG. 13 is a side view of yet another exemplary embodiment of a needle apparatus for delivering one or more occlusion clips including an electrocautery generator coupled to the needle.

Turning to FIG. 13, another embodiment of an apparatus 408 is shown for occluding a vein or other body lumen that generally includes a needle 410 carrying one or more clips (not shown) and a pusher member 430 for delivering the clip(s), generally similar to other embodiments herein. As shown, a hub 450 is provided on a distal end 412 of the needle 410 that includes a side port 452 and source of fluid 454, as described elsewhere herein.

Unlike other embodiments herein, the needle 410 includes one or more electrodes (not shown) on or adjacent the distal tip 415 of the needle 410, and a source of electrical energy, e.g., an electrocautery generator (not shown), which may be coupled to the hub 450 via one or more wires or cables 460. In an exemplary embodiment, the needle shaft 410 may be insulated except for a predetermined length adjacent the distal tip 415, which may be coupled to the generator and cable(s) 460 by one or more internal wires or other conductors (not shown). Alternatively, separate electrodes may be attached around the distal end 414 of the needle 410, which may be coupled to the generator via the cable(s) 460. The apparatus 408 may include a grounding pad (not shown) also coupled to the generator, which may be placed against the patient, e.g., electrically coupled to the patient's skin using known methods. An exemplary embodiment of a generator and/or system that may be used may be found at http://www.boviemedical.com/products_aaron950.asp, the entire disclosure of which is expressly incorporated by reference herein.

During use, the needle 410 may be introduced through the patient's skin and penetrate through a vein 90, similar to other embodiments herein. Once in this position, the generator may be activated to deliver electrical energy, e.g., sixty Watts (60 W) of coagulation energy, to the electrode(s) to cauterize the vein 90 and/or otherwise contract the vein 90 around the distal end 414 of the needle 410. A clip (not shown) may then be deployed from the needle 410, e.g., similar to other embodiments herein.

Figure 14:
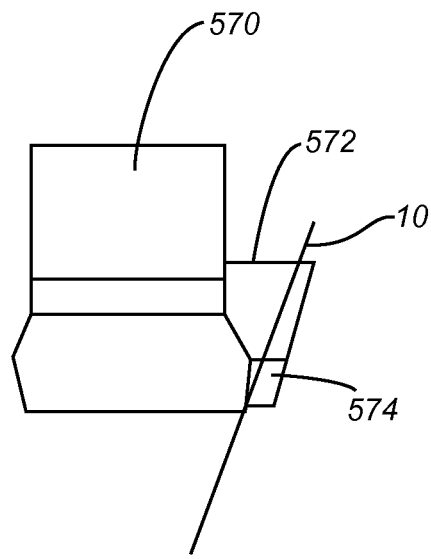
FIG. 14 is a cross-sectional side view of an ultrasound imaging system including a vibrator that may be coupled to a needle apparatus, such as those described herein, to enhance imaging the apparatus during use.

Optionally, in any of the embodiments herein, the needle apparatus may be provided with a imaging system to provide a system for detecting and/or guiding the apparatus during use. For example, as shown in FIG. 14, an ultrasound transducer 570 is shown that includes a needle guide 572 for receiving a needle apparatus 10, which may be any of the embodiments herein. The needle guide 572 may include a vibrator 574, which may be coupled to the needle 10 to vibrate the needle shaft at a predetermined frequency, e.g., between about two and ten Hertz (2-10 Hz) with a velocity of around one meter per second (1.0 m/s). The frequency applied to the needle 10 may correspond to a frequency that enhances detection by the transducer 570 using various modes of the transducer 570, such as motion mode, power mode, amplitude mode, continuous Doppler mode, and the like, as is known to those skilled in the art.

In an exemplary embodiment, the transducer 570 may be placed against a patient's skin and the needle 10 may be loaded through the needle guide 572, e.g., similar to methods used for delivering biopsy needles. As a result, the vibrator 574 may be coupled to the needle 10, which may be configured to vibrate the needle 10 as the needle 10 is penetrated through the skin towards a target vein or other body lumen.

Figure 15A:
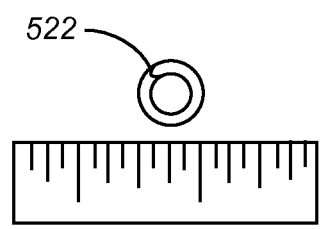
FIGS. 15A and 15B are top and side views of yet another exemplary embodiment of an occlusion clip.
Figure 15B:
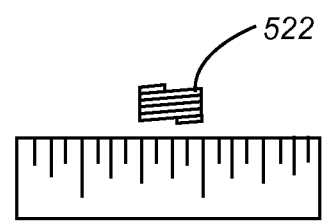

Turning to FIGS. 15A and 15B, another exemplary embodiment of a clip 520 is shown that may be delivered using any of the apparatus described elsewhere herein. As shown, the clip 520 includes a wire or other element wound into a coil, e.g., including a plurality of windings or revolutions, which may be biased to a closed tightly wound shape in which adjacent revolutions may contact one another, as shown, (or may be spaced apart by a first distance), yet may be elastically deformed to facilitate introduction into, through, and/or around a vein or other target body lumen. In an exemplary embodiment, the coil 520 may be stretched axially, e.g., to space apart the revolutions (or increase the spacing to a second distance), and cork-screwed through the vein, e.g., until at least one revolution has passed through to the posterior side of the vein. The coil 520 may then be released, whereupon the revolutions may resiliently compress back towards one another to compress and/or otherwise occlude the vein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for closing a tubular structure within a patient's body, comprising: a tubular member comprising a proximal end including a hub, a distal end including a sharpened distal tip for penetrating through the tubular structure, a lumen having an oblong cross-section extending proximally from the distal end, and defining a longitudinal axis between the proximal and distal ends; a clip compressible between a relaxed state in which a plurality of tines of the clip are shaped to engage and close the tubular structure, and a stressed state in which the plurality of tines are compressed to allow the clip to be loaded into the lumen in a predetermined orientation about the longitudinal axis; and a pusher member comprising a proximal end and a distal end sized for advancement within the lumen for deploying the clip from the distal tip of the tubular member such that the plurality of tines engage and close the tubular structure through which the tubular member is directed, wherein the plurality of tines comprise a pair of distal tines extending from a first end of a central region of the clip and a pair of proximal tines extend from a second end of the central region, the pair of distal tines being substantially shorter than the pair of proximal tines, wherein the pair of distal tines, pair of proximal tines, and the central region define a plane and lie in the plane in the relaxed state, and the pair of distal and proximal tines remain substantially within the plane when the pair of proximal and distal tines are compressed into the stressed state, wherein the pusher member is movable relative to the tubular member from a first position to a second position wherein the pair of distal tines are deployed from the lumen beyond the distal tip, the pair of distal tines resiliently returning towards the relaxed state for engaging a posterior side of the tubular structure through which the distal end of the tubular member is introduced; wherein the tubular member is movable axially relative to the pusher member from the second position to a third position to fully deploy the clip from the lumen beyond the distal tip, the pair of proximal tines resiliently returning towards the relaxed state to surround and engage the tubular structure to compress and close the tubular structure, the apparatus further comprising a stop coupled between the pusher member and the hub to limit movement of the pusher member relative to the tubular member between the first and second positions until the stop is released.

2. The apparatus of claim 1, further comprising one or more features on the hub to provide a visual indication of a rotational orientation of the plane defined by the clip within the lumen.

3. The apparatus of claim 1, wherein the pair of proximal tines curve outwardly from the second end of the central region back towards the first end of the central region in the relaxed state such that, when the tubular member is moved to the third position, the pair of proximal tines expand around and engage the tubular structure.

4. The apparatus of claim 1, wherein the stop is removable from at least one of the pusher member and the hub to allow movement of the tubular member relative to the pusher member from the second position to the third position.

5. The apparatus of claim 1, wherein the pair of distal tines extend from the central region to define opposing hook shapes in the relaxed state.

6. The apparatus of claim 5, wherein the pair of proximal tines are substantially straightened such that the pair of proximal tines are axially aligned with the central region in the stressed state.

7. The apparatus of claim 5, wherein the pair of distal tines are substantially straightened such that the pair of distal tines are axially aligned with the central region in the stressed state.

8. The apparatus of claim 1, wherein the clip further comprises an eyelet adjacent a distal end of the central region.

9. The apparatus of claim 1, wherein the pair of proximal tines are at least partially straightened within the plane when directed to the stressed state for loading into the lumen, and wherein the pair of distal tines are compressed distally away from the pair of proximal tines within the plane when directed to the stressed state for loading into the lumen.

10. An apparatus for closing a tubular structure within a patient's body, comprising: a tubular member comprising a proximal end including a hub, a distal end including a sharpened distal tip such that the tubular member may be directed into-and-through the tubular structure, a lumen extending between the proximal and distal ends, and defining a longitudinal axis between the proximal and distal ends; a clip comprising a pair of proximal tines and a pair of distal tines, the clip compressible between a relaxed state in which the pair of proximal and distal tines are shaped to engage and close the tubular structure, and a stressed state in which the pair of proximal and distal tines are compressed to allow the clip to be loaded into the lumen in a predetermined orientation about the longitudinal axis; and a pusher member comprising a proximal end and a distal end sized for advancement within the lumen for deploying the clip from the distal tip of the tubular member such that the pair of distal tines are deployed initially to partially engage the tubular structure and the pair of proximal tines are deployed subsequently to further engage the tubular structure, the clip resiliently returning towards the relaxed state to substantially close the tubular structure through which the tubular member is directed, wherein the pair of distal tines are shorter than the pair of proximal tines, and wherein the pair of proximal tines at least partially surround the pair of distal tines in the relaxed state such that the pair of proximal tines curve around and engage the tubular structure to close the tubular structure, wherein the pusher member is movable relative to the tubular member from a first position to a second position wherein the pair of distal tines are deployed from the lumen beyond the distal tip, the pair of distal tines resiliently returning towards the relaxed state to at least partially engage the tubular structure through which the distal end of the tubular member is introduced, wherein the tubular member is movable axially relative to the pusher member from the second position to a third position to fully deploy the clip from the lumen beyond the distal tip, the pair of proximal tines resiliently returning towards the relaxed state to further engage the tubular structure to close the tubular structure, and wherein the apparatus further comprises a stop coupled between the pusher member and the hub to limit movement of the pusher member relative to the tubular member between the first and second positions.

11. An apparatus for closing a tubular structure within a patient's body, comprising: a tubular member comprising a proximal end including a hub, a distal end including a sharpened distal tip, a lumen having an oblong cross-section extending proximally from the distal end, and defining a longitudinal axis between the proximal and distal ends; a clip compressible between a relaxed state in which a plurality of tines of the clip are shaped to engage and close the tubular structure, and a stressed state in which the plurality of tines are compressed to allow the clip to be loaded into the lumen in a predetermined orientation about the longitudinal axis; and a pusher member comprising a proximal end and a distal end sized for advancement within the lumen for deploying the clip from the distal tip of the tubular member such that the plurality of tines engage and close the tubular structure through which the tubular member is directed, wherein the plurality of tines comprise a pair of distal tines extending from a first end of a central region of the clip and a pair of proximal tines extend from a second end of the central region, wherein the pair of distal tines, pair of proximal tines, and the central region define a plane and lie within the plane in the relaxed state, and the pair of distal and proximal tines remain within the plane when the pair of distal and proximal tines are compressed into the stressed state, wherein the clip further comprises an eyelet, the apparatus further comprising a filament directed through the eyelet backloaded into the lumen of the tubular member.

12. The apparatus of claim 11, wherein the pair of distal tines extend from the central region to define opposing hook shapes in the relaxed state and wherein the pair of proximal tines extend from the central region such that the pair of proximal tines at least partially surround the central region and the pair of distal tines within the plane in the relaxed state to compress and close the tubular structure.

13. The apparatus of claim 11, wherein the eyelet is located adjacent a distal end of the central region.

14. A apparatus for closing a tubular structure within a patient's body, comprising: a tubular member comprising a proximal end including a hub, a distal end including a sharpened distal tip for penetrating through the tubular structure, a lumen having an oblong cross-section extending proximally from the distal end, and defining a longitudinal axis between the proximal and distal ends; a clip compressible between a relaxed state in which a plurality of tines of the clip are shaped to engage and close the tubular structure, and a stressed state in which the plurality of tines are compressed to allow the clip to be loaded into the lumen in a predetermined orientation about the longitudinal axis; and a pusher member comprising a proximal end and a distal end sized for advancement within the lumen for deploying the clip from the distal tip of the tubular member such that the plurality of tines engage and close the tubular structure through which the tubular member is directed, wherein the plurality of tines comprise a pair of distal tines extending from a first end of a central region of the clip and a pair of proximal tines extend from a second end of the central region, the pair of distal tines being substantially shorter than the pair of proximal tines, and wherein the pair of distal tines, pair of proximal tines, and the central region define a plane and lie in the plane in the relaxed configuration, and the pair of distal and proximal tines remain substantially within the plane when the pair of proximal and distal tines are compressed into the stressed state, and wherein the clip further comprises an eyelet, the apparatus further comprising a filament directed through the eyelet backloaded into the lumen of the tubular member.

* * * * *